United States Patent [19]

Gubelmann et al.

[11] Patent Number: 5,068,391
[45] Date of Patent: Nov. 26, 1991

[54] PREPARATION OF METHYLENEDI (PHENYLURETHANE)

[75] Inventors: Michel Gubelmann; Christophe Rochin, both of Lyons; Christian Allandrieu, Villeurbanne, all of France

[73] Assignee: Rhone-Poulenc Chimie, Courbevoie, France

[21] Appl. No.: 545,547

[22] Filed: Jun. 29, 1990

[30] Foreign Application Priority Data

Jun. 29, 1989 [FR] France .................................. 89 09002

[51] Int. Cl.$^5$ ......................................... C07C 125/073
[52] U.S. Cl. ......................................... 560/25; 560/27
[58] Field of Search ..................................... 560/25, 27

[56] References Cited
U.S. PATENT DOCUMENTS 4,146,727  3/1979  Shawl et al. ........................ 560/25
4,230,877 10/1980  Shawl et al. ........................ 560/25
4,243,815  1/1981  Merger et al. ...................... 560/25
4,282,370 12/1981  Pope ................................. 560/25
4,319,018  3/1982  Miyata et al. ...................... 528/232
4,328,354  5/1982  Merger et al. ...................... 560/25
4,476,317 10/1984  Wada ................................ 560/25
4,543,419  9/1985  Shawl ............................... 560/25

FOREIGN PATENT DOCUMENTS 3202687  8/1983  Fed. Rep. of Germany ........ 560/25

Primary Examiner—Jose G. Dees
Assistant Examiner—Porfirio Nazario
Attorney, Agent, or Firm—Burns, Doane, Swecker & Mathis

[57] ABSTRACT

The bis-(N-carboalkoxyanilino)methanes, optionally in the presence of at least one alkyl N-phenylcarbamate, are selectively rearranged into methylenedi(phenylurethane), MDU, in the presence of an effective amount of hydrofluoric acid.

14 Claims, No Drawings

PREPARATION OF METHYLENEDI (PHENYLURETHANE)

CROSS REFERENCE TO COMPANION APPLICATION

Co-pending application Ser. No. 07/545,502, filed concurrently herewith and assigned to the assignee hereof.

BACKGROUND OF THE INVENTION

1. Field of the Invention

The present invention relates to the preparation of methylenedi(phenylurethane), and, more especially, to the preparation of methylenedi(phenylurethane) by rearrangement of bis-(N-carboalkoxyanilino)methanes.

2. Description of the Prior Art

Methylenedi(phenylurethane), designated MDU, is an intermediate useful in the production of methylenedi(phenyl isocyanate), designated MDI. Indeed, MDU can be pyrolyzed to MDI in a manner known per se. MDI is a particularly useful starting material for the manufacture of polyurethane foams and elastomers.

MDI is conventionally produced by phosgenation of the diamine which results from the condensation reaction of aniline with formaldehyde. The commercial product is a mixture of various isomers of MDI and oligomers, designated polymethylenedi(phenyl isocyanate), PMDI, from which the pure MDI is isolated.

For obvious reasons associated with the toxicity of phosgene and the disadvantages associated with the production of hydrochloric acid during the phosgenation step, numerous attempts have been made to prepare MDI by processes which do not require a phosgenation step.

Thus, various processes for the preparation of MDI from alkyl N-phenylcarbamates have been proposed to this art which comprise a first step entailing a condensation reaction of the N-phenylcarbamate with formaldehyde to form a mixture containing diphenylmethane dicarbamate and polymethylenedi(phenyl carbamate), higher homologs of methylenedi(phenyl carbamate) (or MDU), followed by a thermal decomposition step.

One of the disadvantages presented by this type of process is that the proportion of dinuclear MDI, and in particular of the 4,4'-isomer, is insufficient.

Another disadvantage presented by this type of process is that, during the condensation reaction step, significant proportions of compounds such as N-carboalkoxyanilinophenylmethanes, bis(N-carboalkoxyanilino)methanes and N,N'-dicarboalkoxyaminobenzylanilines, as well as their higher condensation derivatives, are formed together with the desired diphenylmethane dicarbamate. These various impurities are problematical in the conversion of the reaction mixture to the desired diisocyanates.

In U.S. Pat. No. 4,146,727 it has been proposed to rearrange impurities of the N-benzyl type of formula (I):

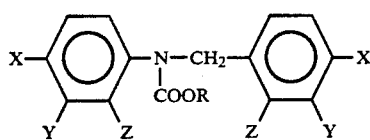

(I)

in which X, Y, or Z can represent in particular, a -NHCOOR group and R is an alkyl group having from 1 to 3 carbon atoms, their dimers, trimers, tetramers, etc., into diphenylmethane dicarbamate by contacting them, at a temperature ranging from 50° to 170° C. and preferably from 80° to 130° C., with a catalytically effective amount of a strong protonic acid medium.

In published French Patent Application No. 2,460,972 (corresponding to U.S. Pat. No. 4,319,018) it is proposed to carry out the step involving the condensation reaction of the alkyl N-phenylcarbamate and formaldehyde, or a precursor material generating formaldehyde, in the simultaneous presence of at least one compound selected, in particular, from among bis(N-carboalkoxyanilino)methanes and N,N'-dicarboalkoxyaminobenzylanilines and an aqueous acid solution, the concentration of which is adjusted such that the reaction kinetics are acceptable and secondary reactions are maintained at a minimum level, at a temperature ranging from 10° to 150° C. and preferably from 20° to 120° C.

This process, however, does not permit the removal of all of the impurities under consideration.

It has now been determined that the N,N'-dicarboalkoxyaminobenzylanilines of the formula:

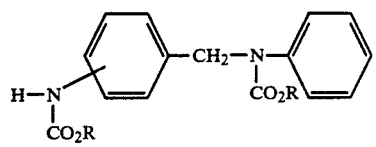

in which R represents an alkyl radical corresponding to the alkyl radical of the alkyl N-phenylcarbamate employed in the condensation reaction with a methylenating agent (compounds containing a methyleneamino linkage), are not only impurities which are difficult to separate, but are also difficult to rearrange to the desired final product, including rearrangement in the presence of an alkyl N-phenylcarbamate. Without wishing to be bound to or by any particular theory, it is considered that the formation of these undesirable impurities resulted from a type of rearrangement of a bis-(N-carboalkoxyanilino)methane corresponding to the formula (II):

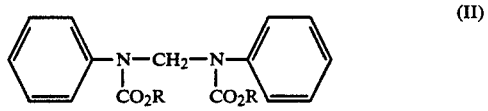

(II)

in which R represents an alkyl radical, under the conditions to date employed during the condensation and/or rearrangement step.

SUMMARY OF THE INVENTION

Accordingly, a major object of the present invention is the provision of an improved process for rearranging the bis-(N-carboalkoxyanilino)methanes of formula (II) into methylenedi(phenylurethane) with enhanced selectivity and to carry out such improved rearrangement with a surprising and unexpected selectivity for the 4,4'-isomer of said methylenedi(phenylurethane).

Briefly, the present invention features a process for the preparation of methylenedi(phenylurethane), comprising rearranging at least one bis-(N-carboalkoxyanilino)methane, if necessary in the presence of at least one alkyl N-phenylcarbamate, wherein such rearrangement is carried out in the presence of hydrofluoric acid.

DETAILED DESCRIPTION OF THE PREFERRED EMBODIMENTS OF THE INVENTION

More particularly according to the present invention, the bis-(N-carboalkoxyanilino)methanes to be rearranged advantageously have the formula (II) given above, in which R represents an alkyl or cycloalkyl radical having from 1 to 6 and preferably from 2 to 4 carbon atoms.

These compounds can be produced by reaction of alkyl N-phenylcarbamate in methylene chloride, which serves both as a solvent for the reaction and as a methylenating agent, in the presence of a 50% sodium hydroxide solution and a phase transfer agent. Cf. *Annales De Ouimica*, ser. C, 80, 255 (1984).

The subject rearrangement can be carried out in the presence of an alkyl N-phenylcarbamate in which the alkyl radical has from 1 to 6 carbon atoms and advantageously is identical to the alkyl radicals in the carboalkoxy groups of the compound of formula (II).

When a carbamate of this type is employed in the reaction mixture, the molar ratio of said carbamate to bis(carboalkoxyanilino)methane, which can vary over wide limits, advantageously ranges from 0.5 to 10 and preferably from 1 to 5.

The subject rearrangement is carried out in the presence of hydrofluoric acid, preferably in the liquid phase. This acid is preferably anhydrous, although the use of a hydrofluoric acid containing water is also within the scope of the invention. The water only slows down the reaction. As the subject rearrangement does not coproduce water, the use of anhydrous hydrofluoric acid will provide an added advantage, namely, the option of facile recycling of such acid.

The amount of hydrofluoric acid to be used is not critical. The hydrofluoric acid can be employed in a significant amount relative to the reactants, such that it constitutes the solvent in the reaction mixture. The hydrofluoric acid can also be present in less amounts.

To advantageously carry out the process of the invention, the molar ratio of hydrofluoric acid to bis-(Ncarboalkoxyanilino)methane is at least 10 and preferably less than or equal to 200. In a preferred embodiment, such ratio will range from 25 to 100.

The reaction temperature, in general, advantageously ranges from $-20°$ to $80°$ C.

Preferably, the process of the present invention is carried out at a temperature ranging from $0°$ to $60°$ C. Indeed, above $60'$ C. a reduction in the proportion of the 4,4'-isomer of methylenedi(phenylurethane), an increase in derivatives containing 3 aromatic rings and an isomerization of the 4,4'-isomer to the 2,4'-isomer are simultaneously observed.

It is also observed, below $60°$ C., that the proportion of derivatives having 3 aromatic rings remains low in the reaction mixture and that, the lower the temperature, the higher is the proportion of the desired 4,4'-isomer in the methylenedi(phenylurethane) produced.

The pressure is not an essential process parameter. However, when the reaction temperature is higher than $20°$ C., it is preferable to operate under a pressure greater than atmospheric pressure in order to maintain the hydrofluoric acid in liquid state.

The process according to the invention can be carried out in hydrofluoric acid as the reaction solvent, or in a mixture of hydrofluoric acid and an organic solvent. Exemplary such organic solvents include aliphatic hydrocarbons such as hexane and heptane; alicyclic hydrocarbons such as cyclohexane and methylcyclohexane; and halogenated hydrocarbons such as chloroform, methylene chloride, ethylene chloride, chlorocyclohexane, perchlorocyclohexane, chlorobenzene and dichlorobenzene. When a solvent of this type is used, it constitutes at most 300% and preferably from 10% to 150% by weight relative to the alkyl N-phenylcarbamate employed.

The reaction time can vary over wide limits; it generally ranges from 15 min to 8 hours.

The reaction can be carried out discontinuously or continuously.

Upon completion of the reaction or of the permitted reaction time, the desired final product is recovered by any appropriate means, for example by evaporation of the hydrofluoric acid.

The process of the present invention is particularly suitable for the rearrangement of bis-(Ncarboethoxyanilino)methane, if necessary in the presence of ethyl N-phenylcarbamate.

In order to further illustrate the present invention and the advantages thereof, the following specific examples are given, it being understood that same are intended only as illustrative and in nowise limitative.

In said examples, the following conventions are used:
(i) MDU YLD (%): represents the yield of methylenedi(ethyl carbanilate) calculated relative to the initial number of moles of —$CH_2$— groups;
(ii) 3-Ph (%): represents the yield (YLD) of compounds having 3 aromatic rings, calculated in like manner;
(iii) 4,4'-: represents methylene-4,4'-di(ethyl carbanilate) of the formula:

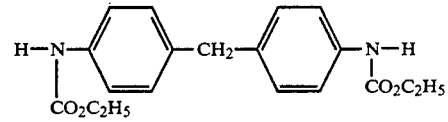

(iv) 2,4'-: represents methylene-2,2'-di(ethyl carbanilate);
(v) A represents bis(N-carboethoxyanilino)methane of the formula:

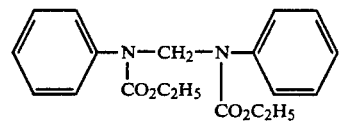

EXAMPLES 1 to 3

The following materials were charged into a Hastelloy reactor having a capacity of 50 cc, fitted with a magnetic stirrer:
(i) 10 mmoles of bis-(carboethoxyanilino)methane (A); and
(ii) 20 g (1 mole) of anhydrous hydrofluoric acid.

After a reaction time of two hours at the temperature (T), the mixture was analyzed by gas phase and liquid phase chromatography.

The particular conditions and the results obtained are reported in Table I below:

The degree of conversion of A was 100% in these examples:

TABLE I

| Example No. | T °C. | MDU Yld (%) | Distribution of isomers (%) 4,4'- | 2,4'- | 3-Ph (%) |
|---|---|---|---|---|---|
| 1 | 40 | 54 | 94 | 6 | 9 |
| 2 | 25 | 58 | 93 | 7 | 10 |
| 3* | 40 | 91 | 93 | 7 | 3 |

*30 mmoles of ethyl phenylcarbamate were added to the charge in this example.

The presence of compounds containing a methyleneamino linkage was not detected in these examples.

EXAMPLES 4 and 5

The following materials were charged into a Hastelloy reactor having a capacity of 50 cc, fitted with a magnetic stirrer:

(i) 30 mmoles of ethyl phenylcarbamate;
(ii) 10 mmoles of bis-(carboethoxyanilino)methane (A);
(iii) x cc of methylene dichloride and (iv) (20-x) cc of anhydrous hydrofluoric acid.

At the end of the experiment, the mixture was analyzed by ga phase and liquid phase chromatography.

The particular conditions and the results obtained after a reaction time of 2 hours at 40° C. are reported in Table II below:

TABLE II

| Example No. | HF (cc) | CH$_2$Cl$_2$ (cc) | MDU YLD (%) | Distribution of isomers 4,4'- | 2,4'- | 3-Ph (%) |
|---|---|---|---|---|---|---|
| 3 | 20 | 0 | 91 | 93 | 7 | 3 |
| 4 | 10 | 10 | ~100 | 94 | 6 | ~1 |
| 5 | 5 | 15 | 97 | 93 | 7 | 3 |

The presence of compounds containing a methyleneamino linkage was not detected in these examples.

The degree of conversion of A was 100% in these examples.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of methylenedi(phenylurethane), comprising rearranging at least one bis-(N-carboalkoxyanilino)methane in the presence of an effective amount of hydrofluoric acid.

2. The process as defined by claim 1, carried out in the further presence of at least one alkyl N-phenylcarbamate.

3. The process as defined in claim 1, carried out in the liquid phase.

4. The process as defined by claim 1, carried out in the presence of anhydrous hydrofluoric acid.

5. The process as defined by claim 2, wherein the molar ratio of the at least one alkyl N-phenylcarbamate to the at least one bis-(N-carboalkoxyanilino)methane ranges from 0.5 to 10.

6. The process as defined by claim 1, said at least one bis-(N-carboalkoxyanilino)methane comprising bis(N-carboethoxyanilino)methane.

7. The process as defined by claim 1, carried out in the presence of an organic reaction solvent.

8. The process as defined by claim 7, said organic solvent comprising methylene chloride.

9. The process as defined by claim 5, said molar ratio ranging from 1 to 5.

10. The process as defined by claim 1, wherein the molar ratio of hydrofluoric acid to the at least one bis-(N-carboalkoxyanilino)methane is greater than or equal to 10.

11. The process as defined by claim 10, wherein the molar ratio of hydrofluoric acid to the at least one bis(N-carboalkoxyanilino)methane is less than or equal to 200.

12. The process as defined by claim 11, wherein the molar ratio of hydrofluoric acid to the at least one bis(N-carboalkoxyanilino)methane ranges from 25 to 100.

13. The process as defined by claim 1, carried out at a temperature ranging from −20° to 80° C.

14. The process as defined by claim 13, carried out at a temperature ranging from 0° to 60° C.

* * * * *